(12) United States Patent
Xiong et al.

(10) Patent No.: US 12,198,468 B2
(45) Date of Patent: Jan. 14, 2025

(54) NON-CONTACT FACIAL BLOOD PRESSURE MEASUREMENT METHOD BASED ON 3D CNN

(71) Applicant: ZHEJIANG NORMAL UNIVERSITY, Jinhua (CN)

(72) Inventors: Jiping Xiong, Jinhua (CN); Zehui Chen, Jinhua (CN); Jinhong Li, Jinhua (CN)

(*) Notice: Subject to any disclaimer, the term of this patent is extended or adjusted under 35 U.S.C. 154(b) by 396 days.

(21) Appl. No.: 17/838,205

(22) Filed: Jun. 11, 2022

(65) Prior Publication Data

US 2023/0005295 A1    Jan. 5, 2023

(30) Foreign Application Priority Data

Jun. 30, 2021 (CN) .......................... 202110731002.8

(51) Int. Cl.
*G06V 40/16* (2022.01)
*A61B 5/021* (2006.01)
*G06F 18/21* (2023.01)

(52) U.S. Cl.
CPC ............ *G06V 40/171* (2022.01); *A61B 5/021* (2013.01); *G06F 18/21* (2023.01); *G06V 40/172* (2022.01)

(58) Field of Classification Search
CPC .... G06V 40/171; G06V 40/172; G06V 10/82; G06V 40/168; G06F 18/21; A61B 5/7221; A61B 5/02108; A61B 5/0033; A61B 5/726; A61B 5/7267; A61B 5/7485; A61B 5/0077; A61B 5/021; A61B 5/02208

See application file for complete search history.

(56) References Cited

U.S. PATENT DOCUMENTS

| | | | |
|---|---|---|---|
| 10,888,256 B2* | 1/2021 | Lee | A61B 5/026 |
| 2021/0007607 A1* | 1/2021 | Frank | A61B 5/14552 |
| 2021/0113093 A1* | 4/2021 | Nozawa | G06V 10/82 |
| 2022/0331028 A1* | 10/2022 | Sternitzke | G05D 1/0094 |

* cited by examiner

*Primary Examiner* — Bobbak Safaipour
*Assistant Examiner* — Michael Kim Maiden

(57) ABSTRACT

A non-contact facial blood pressure measurement method based on 3D CNN is disclosed, which belongs to the technical field of computer vision. The method includes the following steps. S110: collecting an actual face video sample and training a blood pressure prediction model based on face images using 3D CNN neural network. S120: obtaining a face video in real time through a HD camera. S130: recognizing face key points in the face video obtained in S120 through dlib face recognition model, selecting a face region of interest, and extracting face images from the region. S140: performing a wavelet transform operation on the face images extracted in S130 to remove noise. S150: inputting seven consecutive frames of the face images into the 3D CNN blood pressure prediction model trained in S110 to obtain a blood pressure value of the measured person. The disclosure realizes non-contact facial blood pressure measurement.

5 Claims, 2 Drawing Sheets

NON-CONTACT FACIAL BLOOD PRESSURE MEASUREMENT METHOD BASED ON 3D CNN

CROSS REFERENCE TO RELATED APPLICATION

This patent application claims the benefit and priority of Chinese Patent Application No. 202110731002.8 filed on Jun. 30, 2021, the disclosure of which is incorporated by reference herein in its entirety as part of the present application.

TECHNICAL FIELD

The present disclosure relates to the technical field of computer vision, and more specifically, to a non-contact facial blood pressure measurement method based on 3D CNN.

BACKGROUND ART

According to the Report On Cardiovascular Disease In China (2018), the prevalence and mortality of cardiovascular diseases in China are still on the rise. The report estimates that there are 290 million people with cardiovascular diseases, of which hypertension accounts for 245 million. Relevant surveys also show that the mortality of cardiovascular diseases ranks first, higher than that of tumors and other diseases, accounting for more than 40% of residents' disease deaths. Blood pressure refers to the lateral pressure acting on the blood vessel wall per unit area when blood flows in the blood vessel, which changes continuously in each heartbeat cycle. The maximum value of blood pressure is called systolic blood pressure, and the normal range is 90~140 mmHg. The minimum value of blood pressure is called diastolic blood pressure, and the normal range is 60~90 mmHg. The accuracy and real-time of blood pressure value plays an extremely important role in the diagnosis and treatment of hypertension related diseases.

Although the traditional invasive blood pressure measurement has accurate measurement results, and the arterial intubation method is known as the "gold standard", it has been gradually replaced by non-invasive method because of great harm to patients and complex operation. Non-invasive measurement is also divided into intermittent and continuous. Although the products based on the flat tension method can measure the human blood pressure continuously for a long time and the results are more accurate, they need to be positioned in one position for a long time in use. It is difficult for the pressure sensor to ensure that the position will not deviate. At the same time, pressing the wrist for a long time makes the subjects feel uncomfortable. The cuff measurement based on the principle of constant volume method is not convenient for long-term observation of blood pressure, and will compress the arm, which will also produce discomfort.

In recent years, the emergence of photoplethysmography (PPG) provides a new direction for blood pressure measurement. Pulse wave can reflect a lot of information about the subject's cardiovascular function, and theoretically, the formation of pulse is closely related to blood pressure. Non-contact blood pressure measurement has received extensive attention due to the technical requirements of low cost, simplicity and portability, wide application of small semiconductor components.

There are few technical schemes to directly realize blood pressure measurement after image preprocessing by collecting continuous face images based on the strong feature extraction ability of CNN network, especially for the blood pressure measurement based on the temporal dimension characteristics of face region. For example, the patent with Publication No. CN110706826A (A non-contact real-time multi person heart rate and blood pressure measurement method based on video image) uses the second-order differential of the skin color image PPG signals of the whole face as the feature to calculate the blood pressure, without considering the characteristic information of the blood pressure in the time dimension. And in the patent with Publication No. CN111728602A (a non-contact blood pressure measurement device based on PPG), the blood pressure value is obtained by extracting PPG signals in multiple facial regions and then the signals are input into the trained LSTM model. Although this method makes use of timing data information, it does not take into account the characteristics of facial spatial dimension, and it needs to extract and process pulse wave signals, which is cumbersome. Another example is the patent with Publication No. CN110090010A (a non-contact blood pressure measurement method and system). In this method, the three primary color video trace curves of two regions of interest are extracted, and the pulse wave signal is extracted by blind source separation method. This method selects less regions of interest, and has very high requirements for parameters in the calculation method, which is easy to be affected by video frame rate, blind source separation effect, etc.

Because face video contains rich features extracted from temporal and spatial dimensions, it is necessary to propose a non-contact facial blood pressure measurement method that captures the features of temporal and spatial dimensions to improve the accuracy of blood pressure measurement. In order to solve the above problems, a non-contact facial blood pressure measurement method based on 3D CNN is proposed.

SUMMARY

The purpose of the disclosure is to obtain the video images of the face through the camera, detect the key points of the face using the dlib face recognition model, then determine the region of interest through the key points of the face, extract the face images from the region of interest, preprocess the obtained images by wavelet transform, and then input continuous frames of the face images into the trained 3D CNN blood pressure prediction model to obtain the blood pressure value of the measured person, so that the problems raised in the background technology may be solved.

In order to achieve the above purpose, technical solutions of the present disclosure are specifically described as follows.

A non-contact facial blood pressure measurement method based on 3D CNN is provided, which includes the following steps.

S110: collecting an actual face video sample and training a blood pressure prediction model based on face images using 3D CNN neural network.

S120: obtaining a face video in real time through a HD camera.

S130: recognizing face key points in the face video obtained in S120 through dlib face recognition model, selecting a face region of interest, and extracting face images from the region.

S140: performing a wavelet transform operation on the face images extracted in S130 to remove noise.

S150: inputting seven consecutive frames of the face images into the 3D CNN blood pressure prediction model trained in S110 to obtain a blood pressure value of the measured person.

Preferably, the training 3D CNN blood pressure prediction model in S110 includes the following steps.

A1: recording a face video through a HD camera.

A2: obtaining real-time blood pressure values through a cuff electronic sphygmomanometer.

A3: detecting face key points in the face video obtained in A1, selecting a region of interest, and extracting face images of the region of interest.

A4: preprocessing images, that is, performing a wavelet transform operation on the face images extracted in A3 to remove noise, inputting seven consecutive frames of the face images and the corresponding real blood pressure values into a constructed 3D CNN model for training, then training the model based on a mean square error loss function, and finally obtaining the 3D CNN blood pressure prediction model.

Preferably, in S120, when recording the face video of the measured person through the HD camera, the face of the measured person needs to be completely unobstructed. The face video recording needs to be carried out in a bright and stable environment. And at the same time, the face receives light evenly, and there is no obvious dark light area on the face. During the face video recording, the measured person shall keep the body stable, the head shall not shake or tremble, and the face shall be facing the camera until a set collecting time is reached. And in case of large shaking, the recording shall be carried out again.

Preferably, the extracting face images in S130 includes the following steps.

B1: detecting four coordinate extreme values of the face in each frame of the face images through dlib face recognition model to determine a position of the face.

B2: detecting 68 key points of the face, wherein positions of the key points includes chin, eyes, nose, mouth and other regions; and drawing an overall contour of the face through the key points.

B3: determine the region of interest through the key points of the face, which includes the left and right cheeks, forehead, human middle, chin and nasal wing, and extracting and saving an image with a size of 50×50 in each the region of interest.

Preferably, the performing a wavelet transform operation on the face images in S140 includes the following steps.

C1: performing a wavelet transform on the images.

C2: performing a threshold quantization on high-frequency coefficients after hierarchical decomposition.

C3: reconstructing image signals by two-dimensional wavelet.

Preferably, the blood pressure value of the measured person obtained in S150 includes systolic blood pressure and diastolic blood pressure. The obtained blood pressure value is compared with a normal range of the blood pressure to judge whether the blood pressure value of the measured person is in the normal range.

Compared with the prior art, the disclosure provides a non-contact facial blood pressure measurement method based on 3D CNN, which has the following beneficial effects.

(1) The disclosure uses dlib face recognition model to detect the key points of each frame image of the face video, and prevents the position movement of the region of interest caused by face movement or body shaking.

(2) The disclosure makes full use of the function of 3D convolution operation to extract spatial and temporal features from video data for action recognition, and uses 3D feature extractor to operate in spatial and temporal dimensions, so as to capture the motion information of multiple consecutive frames in face video stream.

(3) The disclosure sets a 3D convolution neural network architecture based on 3D convolution feature extraction. The 3D CNN architecture generates multiple information channels from adjacent video frames, performs convolution and down sampling in each channel respectively, and obtains the final feature representation by combining the information from all channels.

DETAILED DESCRIPTION OF THE EMBODIMENTS

The technical scheme in the embodiments of the disclosure will be clearly and completely described below in combination with the attached drawings in the embodiments of the disclosure. Obviously, the described embodiments are only part of the embodiments of the disclosure, not all of the embodiments.

Embodiment 1

Figure 1:
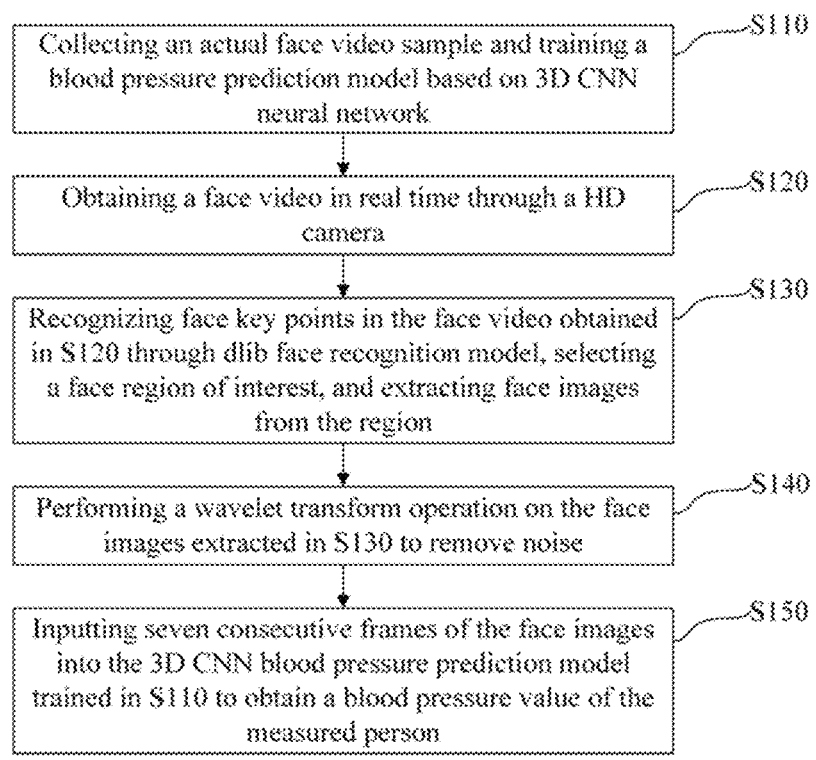
FIG. 1 is a flowchart of the non-contact facial blood pressure measurement method based on 3D CNN proposed by the disclosure.
Figure 2:
FIG. 2 is a schematic diagram of face key point detection of the non-contact facial blood pressure measurement method based on 3D CNN proposed by the disclosure.

Referring to FIG. 1 and FIG. 2, a non-contact facial blood pressure measurement method based on 3D CNN includes the following steps.

S110: collecting an actual face video sample and training a blood pressure prediction model based on face images using 3D CNN neural network.

S120: obtaining a face video in real time through a HD camera.

S130: recognizing face key points in the face video obtained in S120 through dlib face recognition model, selecting a face region of interest, and extracting face images from the region.

S140: performing a wavelet transform operation on the face images extracted in S130 to remove noise.

S150: inputting seven consecutive frames of the face images into the 3D CNN blood pressure prediction model trained in S110 to obtain a blood pressure value of the measured person.

In S120, when recording the face video of the measured person through the HD camera, the face of the measured person needs to be completely unobstructed. The face video recording needs to be carried out in a bright and stable environment. And at the same time, the face receives light evenly, and there is no obvious dark light area on the face. During the face video recording, the measured person shall keep the body stable, the head shall not shake or tremble, and the face shall be facing the camera until a set collecting time is reached. And in case of large shaking, the recording shall be carried out again.

The blood pressure value of the measured person obtained in S150 includes systolic blood pressure and diastolic blood pressure. The obtained blood pressure value is compared with a normal range of the blood pressure to judge whether the blood pressure value of the measured person is in the normal range.

Embodiment 2

The embodiment 2 is based on embodiment 1, but the difference is as follows.

The training 3D CNN blood pressure prediction model in S110 includes the following steps.
- A1: recording a face video through a HD camera.
- A2: obtaining real-time blood pressure values through a cuff electronic sphygmomanometer.
- A3: detecting face key points in the face video obtained in A1, selecting a region of interest, and extracting face images of the region of interest.
- A4: preprocessing images, that is, performing a wavelet transform operation on the face images extracted in A3 to remove noise, inputting seven consecutive frames of the face images and the corresponding real blood pressure values into a constructed 3D CNN model for training, then training the model based on a mean square error loss function, and finally obtaining the 3D CNN blood pressure prediction model.

Specifically, the first layer of 3D CNN architecture is the hardwired layer, which processes the original frames to generate signals of multiple channels, then processes the multiple channels respectively, and finally combines the information of all channels to obtain the final features.

The information of three channels is extracted from each frame, which are grayscale, gradient in x and y directions. The three channels of grayscale, gradients in x and y directions can be calculated per frame, and each channel is convolved using the set convolution kernel to extract different features.

The disclosure makes full use of the function of 3D convolution operation to extract spatial and temporal features from video data for action recognition. By using the 3D feature extractor to operate in the spatial and temporal dimensions, the motion information of multiple consecutive frames in the face video stream is captured.

The disclosure sets a 3D convolution neural network architecture based on 3D convolution feature extraction. The 3D CNN architecture generates multiple information channels from adjacent video frames, performs convolution and down sampling in each channel respectively, and obtains the final feature representation by combining the information from all channels.

Embodiment 3

The embodiment 3 is based on embodiment 1 and 2, but the difference is as follows.

The extracting face images in S130 includes the following steps.
- B1: detecting four coordinate extreme values of the face in each frame of the face images through dlib face recognition model to determine a position of the face.
- B2: detecting 68 key points of the face, wherein positions of the key points includes chin, eyes, nose, mouth and other regions; and drawing an overall contour of the face through the key points.
- B3: determine the region of interest through the key points of the face, which includes the left and right cheeks, forehead, human middle, chin and nasal wing, and extracting and saving an image with a size of 50×50 in each the region of interest.

The disclosure uses dlib face recognition model to detect the key points of each frame image of the face video, and prevents the position movement of the region of interest caused by face movement or body shaking.

Embodiment 4

The embodiment 4 is based on embodiment 1 to 3, but the difference is as follows.

The performing a wavelet transform operation on the face images in S140 includes the following steps.
- C1: performing a wavelet transform on the images.
- C2: performing a threshold quantization on high-frequency coefficients after hierarchical decomposition.
- C3: reconstructing image signals by two-dimensional wavelet.

The above is only the preferred specific embodiments of the disclosure, but the protection scope of the disclosure is not limited to this. Within the technical scope disclosed by the disclosure, the equivalent replacement or change implemented according to the technical scheme and inventive concept of the disclosure by any technician familiar with the technical field shall be covered by the protection scope of the disclosure.

What is claimed is:

1. A non-contact facial blood pressure measurement method based on 3D convolutional neural network (CNN), comprising the following steps:
   S110: collecting an actual face video sample and training a blood pressure prediction model based on face images using 3D CNN neural network;
   S120: obtaining a face video in real time through a HD camera;
   S130: recognizing face key points in the face video obtained in S120 through dlib face recognition model, selecting a face region of interest, and extracting face images from the region;
   S140: performing a wavelet transform operation on the face images extracted in S130 to remove noise; and
   S150: inputting seven consecutive frames of the face images into the 3D CNN blood pressure prediction model trained in S110 to obtain a blood pressure value of the measured person;
   wherein the training 3D CNN blood pressure prediction model in the S110 comprises:
   A1: recording a face video through a HD camera;
   A2: obtaining real-time blood pressure values through a cuff electronic sphygmomanometer;
   A3; detecting face key points in the face video obtained in A1, selecting a region of interest, and extracting face images of the region of interest;
   A4: preprocessing images, that is, performing a wavelet transform operation on the face images extracted in A3 to remove noise, inputting seven consecutive frames of the face images and the corresponding real blood pressure values into a constructed 3D CNN model for training, then training the model based on a mean square error loss function and finally obtaining the 3D CNN blood pressure prediction model.

2. The non-contact facial blood pressure measurement method based on 3D CNN of claim 1, wherein in S120, when recording the face video of the measured person through the HD camera, the face of the measured person needs to be completely unobstructed; the face video recording needs to be carried out in a bright and stable environment, and at the same time, the face receives light evenly, and there is no obvious dark light area on the face; during the face video recording, the measured person shall keep the body stable, the head shall not shake or tremble, and the face shall be facing the camera until a set collecting time is reached; and in case of large shaking, the recording shall be carried out again.

3. The non-contact facial blood pressure measurement method based on 3D CNN of claim 1, wherein the extracting face images in S130 comprises the following steps:
- B1: detecting four coordinate extreme values of the face in each frame of the face images through the dlib face recognition model to determine a position of the face;
- B2: detecting 68 key points of the face, wherein positions of the key points comprises chin, eyes, nose, mouth and other regions; and drawing an overall contour of the face through the key points; and
- B3: determine the region of interest through the key points of the face, comprising the left and right cheeks, forehead, human middle, chin and nasal wing, and extracting and saving an image with a size of 50×50 in each the region of interest.

4. The non-contact facial blood pressure measurement method based on 3D CNN of claim 1, wherein the performing a wavelet transform operation on the face images in S140 comprises the following steps:
- C1: performing a wavelet transform on the images;
- C2: performing a threshold quantization on high-frequency coefficients after hierarchical decomposition; and
- C3: reconstructing image signals by two-dimensional wavelet.

5. The non-contact facial blood pressure measurement method based on 3D CNN of claim 1, wherein the blood pressure value of the measured person obtained in S150 comprises systolic blood pressure and diastolic blood pressure, and the obtained blood pressure value is compared with a normal range of the blood pressure to judge whether the blood pressure value of the measured person is in the normal range.

* * * * *